United States Patent
Arai et al.

(10) Patent No.: US 7,197,107 B2
(45) Date of Patent: Mar. 27, 2007

(54) X-RAY CT APPARATUS AND X-RAY CT METHOD

(75) Inventors: Yoshinori Arai, Tokyo (JP); Masato Wada, Kyoto (JP); Masakazu Suzuki, Kyoto (JP); Hideki Yoshikawa, Kyoto (JP); Takahiro Yoshimura, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 18 days.

(21) Appl. No.: 10/834,519

(22) Filed: Apr. 29, 2004

(65) Prior Publication Data

US 2004/0247069 A1   Dec. 9, 2004

(30) Foreign Application Priority Data

Apr. 30, 2003   (JP) .............................. 2003-125467

(51) Int. Cl.
*A61B 6/04* (2006.01)
(52) U.S. Cl. .............................. 378/20; 378/4; 378/15; 378/38; 378/205
(58) Field of Classification Search ................ 378/20, 378/205, 11, 62, 4, 15, 38–40, 41, 42; 382/131; 345/642, 157–167
See application file for complete search history.

(56) References Cited

U.S. PATENT DOCUMENTS

| | | | | |
|---|---|---|---|---|
| 5,627,868 A | * | 5/1997 | Nobuta et al. | 378/19 |
| 6,041,097 A | * | 3/2000 | Roos et al. | 378/62 |
| 6,243,436 B1 | * | 6/2001 | Hahn et al. | 378/4 |
| 6,309,103 B1 | * | 10/2001 | Sano | 378/205 |
| 6,720,966 B2 | * | 4/2004 | Barth et al. | 345/424 |
| 6,842,502 B2 | * | 1/2005 | Jaffray et al. | 378/65 |

OTHER PUBLICATIONS

David A. Jaffray, Jeffrey H. Siewerdsen, John W. Wong and Alvaro A. Martinez, Flat-panel cone-beam computed tomography for image-guided radiation therapy, International Journal of Radiation Oncology Biology Physics, vol. 53, Issue 5, Aug. 1, 2002, p. 1337-1349.*

* cited by examiner

*Primary Examiner*—Edward J. Glick
*Assistant Examiner*—John M. Corbett
(74) *Attorney, Agent, or Firm*—Koda & Androlia

(57) ABSTRACT

An X-ray computer tomography apparatus wherein a conical X-ray beam is radiated on a local area of an object while a rotary means with an X-ray generator and a two-dimensional X-ray image sensor faced to each other is rotated relative to the object which is disposed between the X-ray generator and the two-dimensional X-ray image sensor. The X-ray computer tomography apparatus comprises a preliminary imaging means for imaging the object under plural positional conditions wherein positional relations among the X-ray generator, the object and the two-dimensional X-ray image sensor are varied, a processing means for obtaining a three dimensional position of a target region of the object by calculating a two-dimensional positional data of a target region of the object which is determined on plural fluoroscopic images obtained by the preliminary imaging means, a position adjustment means for controlling the positional relation among the X-ray generator, the object and the two-dimensional X-ray image sensor in such a manner that the rotary center comes to the three dimensional position obtained by the processing means; and a main imaging means for obtaining a sectional image of the object while the rotary means and the object are relatively rotated after adjusting by the position adjustment means.

6 Claims, 18 Drawing Sheets

X-RAY CT APPARATUS AND X-RAY CT METHOD

BACKGROUND OF THE INVENTION

1. Field of the Invention

The present invention relates to an X-ray CT apparatus in which a conical X-ray beam is radiated on a region of an object to obtain optional tomogram of the part.

2. Prior Art

For obtaining a tomogram of a target region of an object (patient and so on) by means of a conical beam type X-ray CT (computed Tomography) apparatus, a local radiography is executed such that the target region is extremely limited. Therefore, it is required to determine the target region in advance in order to accurately include the target region to be imaged in the projection area. In the prior art the target region has been determined by the following method.

At first, CT imaging is executed, and then plural fluoroscopic images for specifying a reconstruction position, namely for specifying a target region, are obtained in order to reconstruct a tomogram (CT image). A desired fluoroscopic image is picked up among the obtained plural fluoroscopic images and a three-dimensional position of the target region is determined based on the fluoroscopic image that has been picked up. Then, the region around the determined position is reconstructed, thereby obtaining a tomogram of the target region. Such an X-ray CT method is disclosed in JP-A-2001-292991.

According to such a prior art, the tomogram of a relatively large area such that the target region is included in the projection area is obtained, and then the target region is found out among the fluoroscopic images which have been obtained by CT scan on a large area, and the position to be reconstructed as a tomogram is obtained.

In this method, because the imaging apparatus for a large area is required and the fluoroscopic images in a large area are required to be obtained, the X-ray exposed dose is tends to be increased and the X-ray CT apparatus becomes to be large scaled. Therefore, there is a room for improvement in downsizing the apparatus and in expediting imaging by reducing the time required for obtaining tomograms.

SUMMARY OF THE INVENTION

The object of the present invention is to provide a small scale X-ray CT apparatus in which a conical X-ray beam suitable for local radiography is used, the target region is accurately determined with a relatively short time, and its X-ray exposed dose is reduced.

According to the X-ray computer tomography apparatus of the first aspect of the present invention, a conical X-ray beam is radiated on a local area of an object while a rotary means with an X-ray generator and a two-dimensional X-ray image sensor faced to each other is rotated relative to the object which is disposed between the X-ray generator and the two-dimensional X-ray image sensor. The X-ray computer tomography apparatus comprises a preliminary imaging means for imaging the object under plural positional conditions wherein positional relations among the X-ray generator, the object and the two-dimensional X-ray image sensor are varied each other; a processing means for obtaining a three dimensional position of a target region of the object by calculating a two-dimensional positional data of the target region of the object which is determined on plural fluoroscopic images obtained by the preliminary imaging means; a position adjustment means for adjusting the positional relation among the X-ray generator, the object and the to-dimensional X-ray image sensor in such a manner that the rotary center comes to the three dimensional position obtained by the processing means; and a main imaging means for obtaining a tomogram of the object while the rotary means and the object are relatively rotated after adjusting with the position adjustment means.

According to the above-mentioned construction, the fluoroscopic images are obtained in at least two-way positional relation among the X-ray generator, the object and the two-dimensional X-ray image sensor, such that at the front and the side of the object, before CT imaging. Therefore, the target region is determined in the two fluoroscopic images and the three-dimensional position of the target region that is an object of CT imaging is accurately determined. The rotary center comes to the three-dimensional position of the obtained target region by the position adjusting means and the rotary means and the object are relatively rotated, thus executing CT imaging. Therefore, the tomogram of a desired position is obtained while the target region and the like is accurately positioned.

For example, determining a target region on a fluoroscopic image, the three-dimensional image of the straight line formed by the X-ray beam passing the target region on the displayed fluoroscopic image when at least one target region is specified. On the other fluoroscopic image obtained by changing the projection area, the three-dimensional data of the straight line is similarly calculated. A principle is applied such that the three-dimensional position of the target region is automatically calculated by arithmetic operation from the intersections of all the straight lines. As a result, a target region to be projected is accurately determined by means of at least two fluoroscopic images, then X-ray CT imaging is executed, so that an X-ray CT apparatus in which positioning is accurately and rapidly done by a little preliminary projecting and tomograms on a desired region are effectively obtained in a short time.

According to the second aspect of the present invention, the X-ray computer tomography apparatus further comprises a proportion modification means capable of changing the proportion of the distance between the object and the two-dimensional X-ray image sensor to the distance between the X-ray generator and the two-dimensional X-ray image sensor; and a proportion setting means for making the proportion at the time of obtaining a tomogram smaller than at the time of obtaining a fluoroscopic image.

In the above-mentioned construction, the proportion of the distance between the object and the two-dimensional image sensor is smaller than the distance between the two-dimensional X-ray generator and the X-ray image sensor is set smaller in case of obtaining a fluoroscopic image for positioning rather than in case of obtaining a tomogram by X-ray CT, thus the fluoroscopic image becomes reduced than the tomogram. Therefore, the whole area to find out the target region like a diseased region of an object is made larger. Accordingly, only one fluoroscopic image is required for obtaining the fluoroscopic image on which the target region exists without obtaining plural fluoroscopic images by changing the positional conditions, thereby preventing obtaining unnecessary fluoroscopic images and enabling to efficiently obtain the fluoroscopic image on which the target region exists. Thus, the function and effect of the first aspect of the present invention can be reinforced.

According to the third aspect of the present invention, the X-ray computer tomography apparatus further comprises a scan imaging means for shifting said two-dimensional X-ray image sensor in a direction orthogonal to the conical X-ray beam radiated from said X-ray generator while said preliminary imaging means is imaging a fluoroscopic image.

According to the above-mentioned construction, the X-ray generator and the two-dimensional image sensor are slid in a direction orthogonal to the radiated conical X-ray beam, preferably in a crosswise direction that is horizontal or in a vertical direction that is perpendicular. The fluoroscopic image area is practically enlarged while the distance between the X-ray generator and the two-dimensional image sensor is substantially kept, so that the whole area to find out a target region like a diseased region of an object becomes large. Therefore, as mentioned above, unnecessary fluoroscopic images are prevented from being obtained and the fluoroscopic image including the target region is efficiently obtained, thereby reinforcing the function and effect of the first aspect of the present invention.

According to the forth aspect of the present invention, the X-ray computer tomography apparatus further comprises a display means for showing plural fluoroscopic images on a screen in array; and a positioning operation means for specifying the three-dimensional position in such a manner that a target region is first directed on any one of fluoroscopic images shown on the display means with one cursor in the crosswise and/or vertical direction then the target region is secondary directed on another fluoroscopic images other than the one fluoroscopic image with other cursor in the vertical and/or crosswise direction.

According to the construction mentioned above, the target region is determined while displaying a fluoroscopic image by means of a display means such as a liquid crystal display. When an either one cursor in the vertical or crosswise direction is specified on one fluoroscopic image, the two-dimensional position of the target region is determined, and when other cursor in the vertical or crosswise direction is specified on the other fluoroscopic image, the three-dimensional position thereof is determined. Popular equipment like a personal computer can easily specify (point) the target region by means of a well-known cross cursor in the vertical and horizontal direction, thereby assuring facility and convenience.

According to the fifth aspect of the present invention, the X-ray computer tomography apparatus further comprises an image storing means in which plural fluoroscopic images for determining a target region and a tomogram at the target region obtained by these fluoroscopic images are associated and stored; a display means; and an image invocation means having a function for displaying the tomogram of the specified target region on said display means when that target region is specified on the fluoroscopic image selected of those stored in said image storage means is displayed on said display, and/or a function for displaying the fluoroscopic image which is used for obtaining the position of the displaying tomogram while the tomogram selected from the tomograms stored in said image storage means is displayed on said display means.

According to the above-mentioned construction, plural fluoroscopic images before CT imaging and the tomogram obtained by CT imaging after having been positioned are linked, namely they are correspondingly associated and stored. Further, when either one of the linked fluoroscopic image or the tomogram is specified, its corresponding image is automatically searched and is invoked, so that the relating image is rapidly searched, thereby assuring feasibility. For example, the tomogram of internal ear is displayed on the display means, the two or more fluoroscopic images that have been used for positioning are searched and displayed by a click operation. Or when two fluoroscopic images are selected and displayed, the tomogram of the region that is positioned by these fluoroscopic images is searched and displayed by a click operation.

According to the sixth aspect of the present invention, the X-ray computer tomography apparatus further comprises a control means for indicating a projection area specified by a three-dimensional position on the fluoroscopic image displayed on said display means when that three-dimensional position is obtained.

According to the above-mentioned construction, when the three dimensional position of the target region is obtained from plural fluoroscopic images, the projection area of the tomogram by CT imaging relating to the target region is simultaneously displayed at this time. Therefore, without waiting for the image reconstructed after CT imaging, namely without seeing the tomogram, the projection area of the tomogram is understood at the time when the target region is determined, thereby being convenient. For example, when the tomogram area is large, the CT imaging ratio is reduced in advance, or when the tomogram area is small, the CT imaging ratio is enlarged in advance. Therefore, there is an advantage such that re-projection after finishing CT imaging is prevented from occurring in advance.

According to an X-ray computer tomography method of the present invention, a conical X-ray beam is radiated on a local area of an object while a rotary means with an X-ray generator and a two-dimensional X-ray image sensor faced to each other is rotated relative to the object which is disposed between the X-ray generator and the two-dimensional X-ray image sensor. The X-ray computer tomography method comprising the steps of imaging said object under plural positional conditions wherein positional relations among said X-ray generator, said object and said two-dimensional X-ray image sensor are varied; obtaining a three dimensional position of a target region of said object by calculating a two-dimensional positional data of a target region of said object which is determined on plural fluoroscopic images obtained by said preliminary imaging means; adjusting said positional relation among said X-ray generator, said object and said two-dimensional X-ray image sensor in such a manner that the rotary center comes to said three dimensional position of a target region of said object obtained by said processing means; and obtaining a tomogram of said object while said rotary means and said object are relatively rotated after adjusting with said position adjustment means.

According to the above-mentioned method, the construction of the first aspect is made to a method and the same function and effect can be obtained.

BRIEF DESCRIPTION OF THE DRAWINGS

FIG. 1 shows an external view of an X-ray CT apparatus.

FIG. 4a shows positioning by a cursor in the crosswise direction, and FIG. 4b shows positioning by a cursor in the vertical direction.

FIG. 5a shows positioning by a cursor in the crosswise direction, and FIG. 5b shows positioning by a cursor in the vertical direction.

DETAILED DESCRIPTION OF THE INVENTION

Figure 1B:
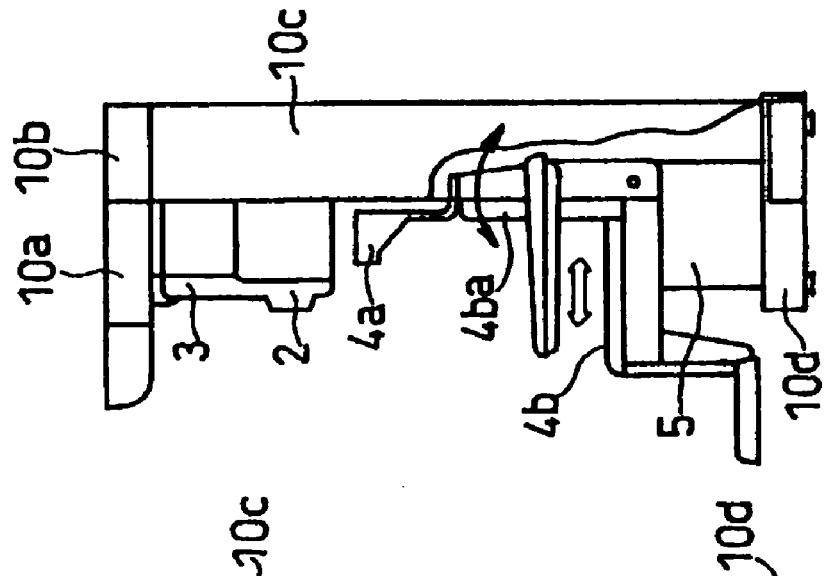
FIG. 1a is its front view and FIG. 1b is its side view.
Figure 2:
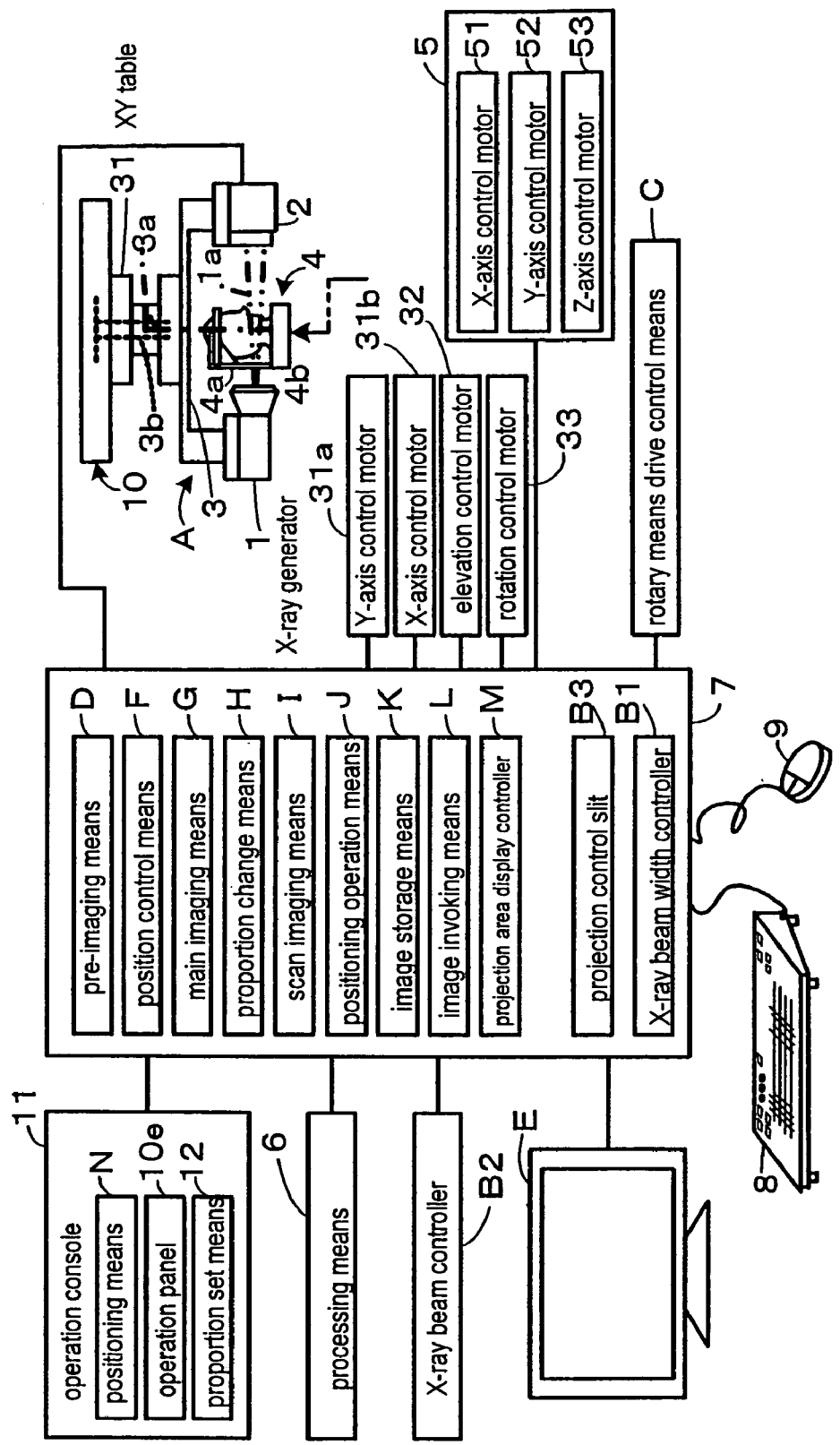
FIG. 2 shows a basic construction of an X-ray CT apparatus.
Figure 3:
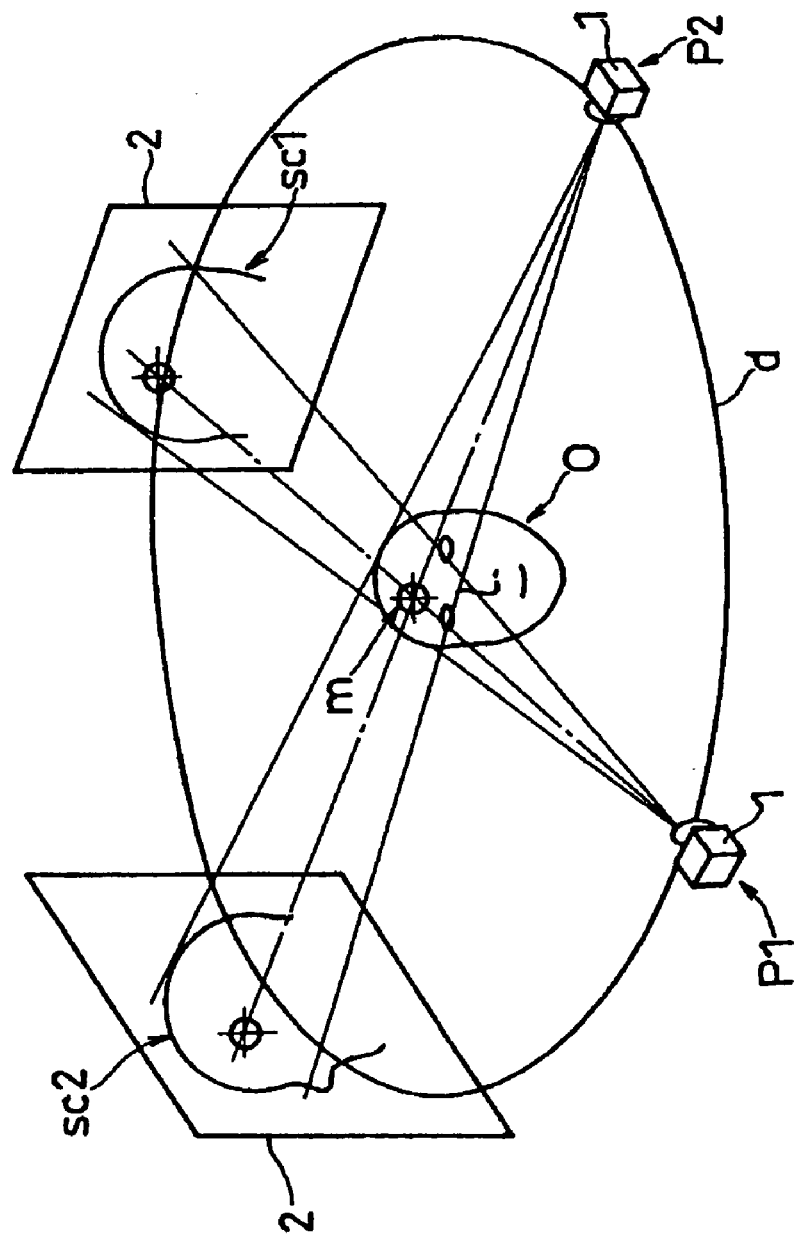
FIG. 3 shows how a scout image is made.

The preferred embodiments of the present invention are explained referring to the attached drawings. FIG. 1 shows a front view and a side view showing the external appearance of an X-ray CT apparatus of the present invention. FIG. 2 shows its basic construction. FIG. 3 is a conceptual view showing a principle of a positioning method. The reference numeral "d" in FIG. 3 and FIG. 7 indicates a rotary movement trace of a rotary means 3.

According to the X-ray CT apparatus 20 as shown in FIG. 1 and FIG. 2, a main frame 10 which is a gate type structure with high rigidity is constructed as a support member for the entire system. The main arm 10 is comprised of a rotary arm 10a for rotatably supporting a rotary means 3 from which an X-ray generator 1 and a two-dimensional X-ray image sensor 2 are opposed and suspended, a pair of cross beams 10b for fixedly holding the base end of the arm 10a, a pair of longitudinal beams 10c for supporting the cross beams 10b, a base 10d on which the pair of longitudinal beams 10c are fixed and which constitutes a base of the apparatus 20.

A highly rigid steel material is used for the members of the main frame 10 and braces and angular reinforcing members are appropriately used for resisting deformation so as not to vary the rotation center 3a of the rotary means 3 during rotation. Thus the main frame 10 is constructed not to cause the rotary deflection of the rotary means 3, so that it is applicable for the X-ray CT apparatus which requires no rotary deflection.

An operation panel 10e is provided where an operator easily handles while standing on the surface of one longitudinal beam 10c of the main frame 10. A chair 4b of an object holding means 4 is placed on an object moving means 5 that is explained later referring to FIG. 3. The chair 4b is moved in X, Y, or Z direction, namely in front and back, right and left, or up and down directions, and the head of an object O is inclined and held by tilting a backrest 4a of the chair 4b.

Next a basic construction of the X-ray CT apparatus is explained. As shown in FIG. 2, the X-ray CT apparatus 20 is provided with a control means 7 which is a personal computer serving as a base of all operations, an X-ray imaging means A, an X-ray beam control means B, a drive control means for a rotary means C, a processing means 6, a display monitor such as a liquid crystal display (one example of display means) E, the object holding means 4 for fixing and holding the object O, the object position moving means 5 for moving the object holding means 4, the main frame 10, an operation console 11, the operation panel 10e and the like. The reference numeral 8 indicates a keyboard and 9 indicates a mouse.

The X-ray imaging apparatus A has the rotary means 3 from which the X-ray generator 1 and the two-dimensional X-ray image sensor 2 are opposed and suspended. The rotary means 3 may be a rotary arm as shown in the figure or a well-known gantry for projecting a patient on a horizontal plane. The rotary means 3 may be any shape that is rotated while opposing the X-ray generator 1 and the two-dimensional X-ray image sensor 2. The X-ray beam control means B comprises an X-ray beam width restriction means B1, an X-ray beam controller B2, and a radiation control slit B3. The X-ray beam radiated from an X-ray tube is controlled by the X-ray beam width control means B1 so as to radiate a conical X-ray beam 1b with a desired beam width. The X-ray beam control means B may be provided for the X-ray generator 1. The conical X-ray beam 1a described herein may be like a circular cone or a pyramid.

For obtaining a fluoroscopic image, mentioned later, by the X-ray beam controller B2, X-ray beam with a large section should be radiated, and for obtaining a tomogram by the X-ray CT imaging mentioned later, X-ray beam with a small section should be radiated. As a result, a fluoroscopic image with a wide area is obtained as for a fluoroscopic image with relatively small X-ray exposure dose, and only an interested area is radiated for obtaining a tomogram in which X-ray is sequentially radiated and is subjected to relatively large X-ray exposure dose, thereby assuring diagnosis efficiency and reducing X-ray exposure dose. A sensor for a wide area such as an X-ray MOS sensor and the like improves the efficiency.

In the two dimensional X-ray image sensor 2, the X-ray runs into a scintillator layer formed on the surface of X-ray Image Intensifier (X-ray II) to be converted into a visible light, the visible light is converted to electron with a photoelectric transducer to be multiplied, the multiplied electron is converted into a visible light by a fluorescent substance to be photographed with a two-dimensionally arranged CCD (charge coupled device) camera via a lens. The two-dimensional X-ray image sensor 2 includes an X-ray TFT (Thin Film Transistor) sensor, an X-ray MOS (Metal Oxide Semiconductor) sensor, an X-ray II (Image Intensifier) camera, an X-ray amorphous selenium sensor, an X-ray CCD (Charge Coupled Device) sensor, an X-ray CCD sensor with amplifier (XICCD) other than the mentioned above.

The object holding means 4 has a chair 4b for holding an object (patient) O at sitting position and a head fixing means 4a provided at the back of the chair 4b. The object position moving means 5 has an X-axis control motor 51 for moving the object holding means 4 in X-direction which is a horizontal direction in FIG. 1a when seen from the front, a Y-axis control motor 52 for moving the object holding means 4 in Y-axis direction which is a back and forth direction in FIG. 1a when seen from the front, and a Z-axis control motor 52 for moving the object holding means 4 in Z-direction which is an up and down direction in FIG. 1a when seen from the front.

X-axis, Y-axis, and Z-axis liner motion tables (not shown) driven by these motors respectively comprise a well-known cross roller guide or a combination of a general bearing and guide capable of accurate liner motion. Movement of these X-axis, Y-axis and Z-axis liner motion tables by means of these motors 51–53 may employ a rack-and-pinion type, a ball screw type, or a general screw axis type. It is desirable to employ one capable of accurate positioning.

The object O sits on the chair 4b, the head fixing means 4a holds the head of the object O, and the object position moving means 5 is used to meet the center of the local area in the object O with the rotary center 3a of the rotary means 3. If a gantry is used for the rotary means 3, the object holding means 4 is formed like a bed because the object O usually lays thereon, is designed to move three-dimensionally in X-direction which is a horizontal direction, in Y-direction which is a back and forth direction, and in Z-direction which is an up and down direction when seen from the front when the object is laid on the bed with his face up. That is, the rotary means may be rotated on a horizontal plane around an objective projection area of the patient sitting on a chair or standing like the embodiment of the present invention or the rotary means may be rotated on a vertical plane around an objective projection area of the patient laying on a bed.

In the above-mentioned embodiment, the object's position is arranged while the rotary means 3 is fixed and the object holding means 4 is moved. On the other hand, instead of moving the object holding means 4 with the object position moving means 5, the object holding means 4 may be fixed without moving any direction like X, Y, Z, the rotary means 3 may be moved by means of an XY table 31 and an elevation control motor 32, mentioned later, so as to agree the rotary center 3a of the rotary means 3 with the center of the local area in the object O. Of course, positional arrangement may be executed by multiply moving both of the object holding means 4 and the rotary means 3.

Figure 1A:
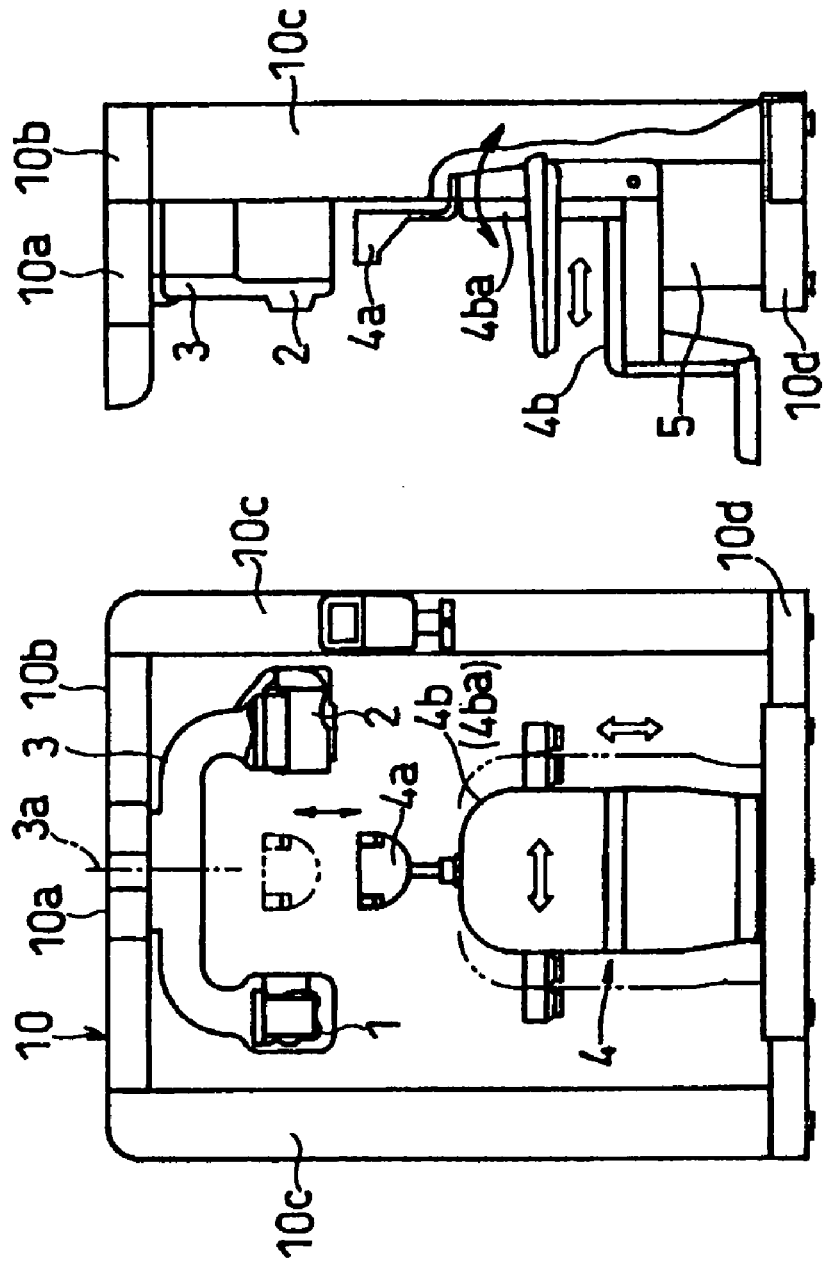

The rotary means 3 is provided with the XY table 31 movable in directions orthogonal each other on a horizontal plane, the X-axis control motor 31a for moving the XY table 31 in X-direction which is right and left direction when seen from the front in FIG. 1a, the Y-axis control motor 31b for moving the XY table in Y-direction orthogonal to the X-direction, the elevation control motor 32 for moving the rotary means 3 up and down when seen from the front in FIG. 1a, and a rotation control motor 33 for rotating the rotary means 3. Controlling the X-axis control motor 31a and the Y-axis control motor 31b, the rotary center 3a of the rotary means 3 is adjustable in its position in XY direction, the elevation motor 32 is driven to go the rotary means 3 up and down, and the rotation control motor 33 is driven at a constant velocity on imaging to rotate the rotary means 3 around the object O. Thus, the elevation control motor 32 constitutes an up and down position control means of the arm of the rotary means 3.

The rotary center 3a of the rotary means 3, namely a pivot, is vertically provided, the rotary means 3 is rotated horizontally, and conical X-ray beam is locally radiated horizontally, thereby constructing a vertical type apparatus with small occupied area. The rotation control motor 33 constitutes a rotary drive means of the rotary means 3, employs a motor such as a servo motor of which rotational speed and rotational positions are freely controlled, and is directly connected to the rotary center 3a of the rotary means 3 via the axis.

Therefore, the rotary means 3 can be rotated at a constant velocity or a variable velocity, and further its rotational position can be known along a time axis, thereby being convenient for taking out an X-ray transmitted image with the two-dimensional X-ray imaging sensor 2 in exact timing. In addition, it doesn't cause any runout, so that local X-ray CT imaging is effectively executed.

A hollow part 3b is provided at the rotary center 3a of the rotary means 3. In order to provide such a hollow part 3b, it is required to provide a hollow part for all the parts mounted on the rotary center 3a. For example, a servo motor with a hollow axis may be employed for its purpose as the rotation control motor 33. The hollow part 3b is provided for arranging wiring between the X-ray generator 1, the two-dimensional image sensor 2, both being suspended from the rotary means 3, and the operation console 11 provided for the main frame 10.

For providing electric wiring for a rotating member, its arrange method is problematic. When the connection wire is provided via the rotary center 3a of the rotary means 3, the affect of twist caused by rotation is made minimum and further preferable appearance is obtained. The position control means 31 constructed with the XY table, the elevation control motor 32, the rotation control motor 33 are combined to constitute the drive control means for a rotary means C in this embodiment. However, the present invention isn't limited to such an embodiment. In the simplest construction, the center 3a of the rotary means 3 may be set at an optional position by manipulating a handle with a hand.

In this apparatus 20, both the object position moving means 5 for moving the object side and the XY table 31 and the elevation control motor 32 for moving the rotary means 3, which is a radiation side, are provided. However, either one of them may be provided. In case of local X-ray CT imaging, it is important not to cause runout of the rotary center 3a, so that it is preferable that the rotary means 3 is rotated during projection, on the other hand the rotary center 3a is fixed.

The processing means 6 has an arithmetic processor capable of high-speed image processing analysis. The X-ray transmitted image produced on the two-dimensional image sensor 2 is pre-processed, a predetermined arithmetic operation is executed to calculate a three-dimensional X-ray absorption coefficient data in the object through which X-ray is transmitted. Further, operation such as projection of the obtained data on a projection plane is executed to three-dimensionally display the projection image and the X-ray image on an external display means, and those images are stored in a storage means as image information.

Next, a method for positioning a target region in case of CT imaging is explained. The X-ray CT apparatus 20 of the present invention has a preliminary imaging means D for projecting the object O under plural positional conditions in which the positional relation among the X-ray generator 1, the object O and the two-dimensional X-ray image sensor 2 is different, the processing means 6 for obtaining the three-dimensional position of the target region in the object O by calculating a two-dimensional data of the target region of the object O which is artificially determined on the plural fluoroscopic images obtained by the preliminary imaging means D, a position control means F for controlling the position of the X-ray generator 1, the object O and the sensor 2 in such a manner that the rotary center 3a comes to the three-dimensional position obtained by the processing means 6, and the main imaging means G for obtaining the tomogram of the object O while relatively rotating the rotary means 3 and the object 3.

The target region means an intended target region for specifying the position to be pictured. The target region "e" in this specification may be specified with a fixed area or one point. It is preferably a rough standard for specifying the object to be photographed in this specification. When a specific point is employed as the target region as an intended target, it is called as a target point in this specification. The reference numeral "m" in this specification indicates this target point. The target point "m" is preferably specified in the projection area, more preferably at the center of the projection area.

As shown in FIG. 3, the target region is roughly determined by controlling the chair 4b. Specifically, the head of the object O is positioned between the X-ray generator 1 and the two-dimensional X-ray image sensor 2. The X-ray generator 1, the object O and the sensor 2 are positioned, for example, like a first positional relation P1 in which a conical X-ray beam is radiated from the front of the head through its back and a first fluoroscopic image (it is called as a scout image hereinafter) sc1 is obtained.

Then the rotary means 3 is rotated with an appropriate angle (for example, 90 degrees) to set a second positional relation P2 in which a conical X-ray beam passes through from the left side to the right side of the head and a second scout image sc2 is obtained at this situation. These scout images sc1 and sc2 are accordingly stored in an image storage means K. The imaging at these two times is executed by means of the preliminary imaging means D operated by the operation panel 10e.

Figure 4:
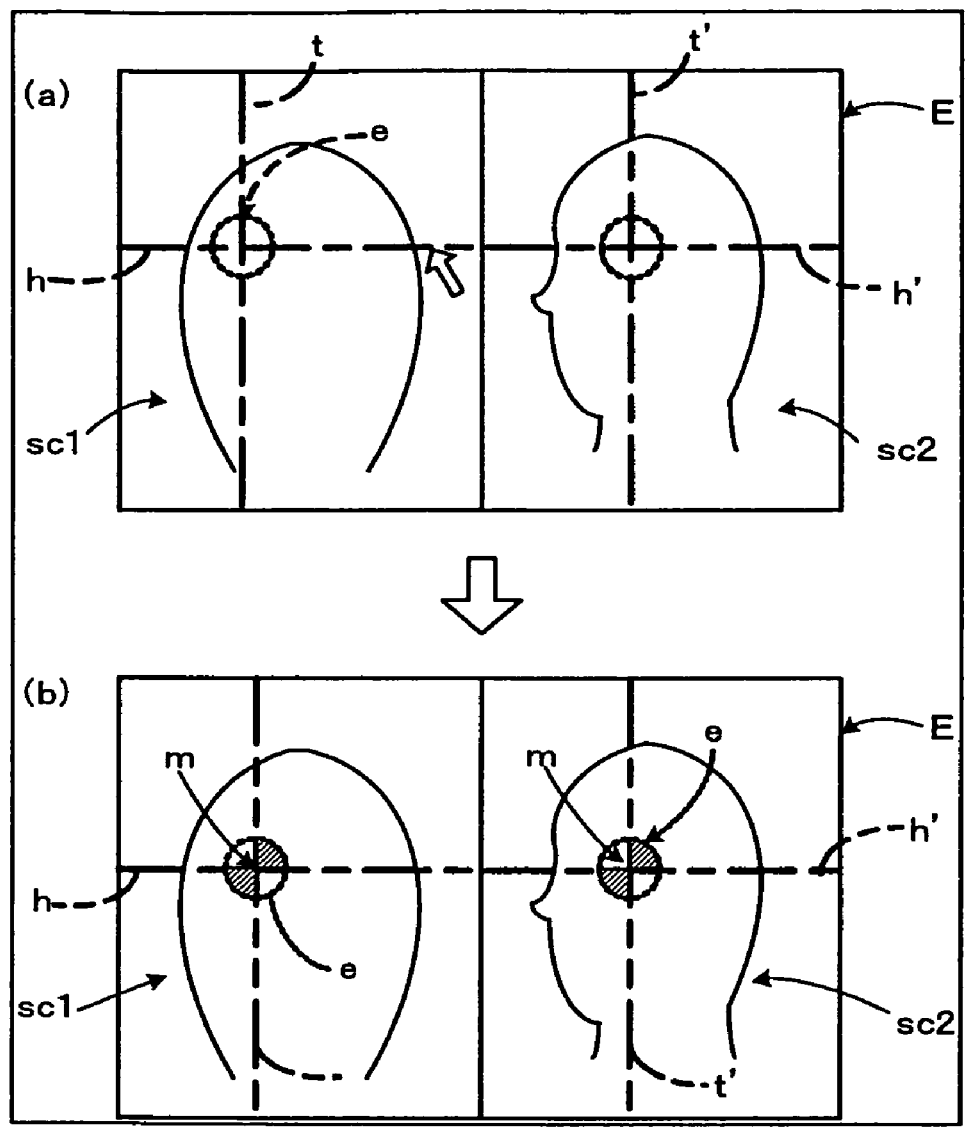
FIG. 4 shows how the CT projection position is determined on a display monitor.

The obtained scout images sc1 and sc2 are displayed on a display monitor E at right and left as shown in FIG. 4. When a cursor is moved and clicked at around the center of the target region "e" which seems to a diseased part of the patient by means of a mouse 9 on the first scout image sc1 displayed on the left in FIG. 4a, a horizontal position "h" which is an up and down direction and a longitudinal position "t" which is a right and left direction are specified. At this time, the longitudinal position t' is displayed at the center as an initial position and a horizontal position h' is displayed at a position corresponding to the side position "h" on the first scout sc1 obtained by calculation on the second scout image.

Next, the cursor is moved to the second scout image sc2 as shown in FIG. 4a and is moved to around the center of the target region "e" on the second scout image sc2. When the mouse is clicked at the position, namely a target point "m", the vertical positions t, t', which are right and left direction, are specified and a three-dimensional potion of the target point "m" is artificially determined. These series of positioning operations are done by a positioning operation means J. This longitudinal position is simultaneously displayed on the first scout image sc1 that is arrayed on the screen, so that when both of the longitudinal and vertical positions are clicked, a display showing the three-dimensional position of the target point "m" is determined is shown on both scout images sc1 and sc2.

As mentioned above, after finishing specifying the three-dimensional position of the target point "m", the data is calculated in the processing means 6 to perform the position control means F such that the center of projection position by means of the X-ray imaging means A, namely the rotary center 3a of the rotary arm 3, becomes to the target point "m". The X-axis control motor 51, the Y-axis control motor 52, the Z-axis control motor 53 are controlled to adjust the position of the chair 4b. Or the X-axis control motor 31a, the Y-axis control motor 31b, or the elevation control motor 32 may be driven and controlled so as to adjust the position of the rotary means 3 without providing the position control motor for the chair 4b.

A display such as "target point set completed" is shown on the display monitor E on finishing positioning of the target point, and after confirming it, the main imaging means G is driven by means of the operation panel 10e, thereby executing CT imaging. The image obtained by this CT imaging is reconstructed with the processing means 6 and so on after completing imaging, and the reconstructed image, namely a tomogram, obtained by the CT imaging is stored in the image storage means K while being linked (related) with two scout images sc1, sc2 which have been obtained in order to determine the position of the target point "m" in advance.

As mentioned above, the preliminary imaging means D comprises at least the X-ray generator 1, the object holding means 4, the two-dimensional X-ray image sensor 2 and the rotary means 3 and the main imaging means G comprises the processing means 6, the position control means F other than the preliminary imaging means D.

Preliminary imaging is thus executed using scout images and CT imaging can be rapidly and efficiently carried out at an intended position while accurately determining a target region. Obtained plural scout images and CT images are stored in the control means 7. With a keyboard 8 and the mouse 9 of a personal computer, the CT images which have been obtained on some date are invoked, one of them is clicked and selected if there are several CT images, and the display "scout!" is shown at a position like the lower right corner on the screen of the display monitor E on which the selected CT image is shown.

When a cursor is moved to the display "scout!" and is clicked with the mouse 9, two (or more) scout images sc1 and sc2 used for positioning of the displayed CT image are simultaneously shown on the upper left of the screen of the display monitor E. When the scout image shown at a small scale is clicked at this situation, the scout images sc1 and sc2 are displayed at full screen size on the display monitor E in a manner that the scout images are arranged in an array side by side, while the CT image is displayed on the upper left in a small size. Thus images should be shown in a reversed size relation, thereby being convenient. These series of operations are controlled by the image storage means K and an image invoking means L provided for the control means 7.

Next, a proportion setting means 12 is explained. As shown in FIG. 2, a proportion change means H variable of the relative proportion of the distance between the object O and the two-dimensional X-ray image sensor 2 to the distance between the X-ray generator 1 and the two-dimensional image sensor 2 is provided for the control means 7 and the proportion setting means 12 is provided for the operation panel 11 such that the relative proportion becomes small in case of obtaining a scout image rather than obtaining a tomogram.

Namely, for setting a target region on a scout image, it is preferable to be selected from a projection area as large as possible because of its working property. However, in case of a local X-ray CT imaging apparatus 20 preferable to dental use or otolaryngologic use, its projection area is originally small. It is advisable to project a wide area of the object O in case of obtaining a scout image for seeking and determining the target region. Under these circumstances, a scout image only on a relatively small area is obtained.

Figure 6:
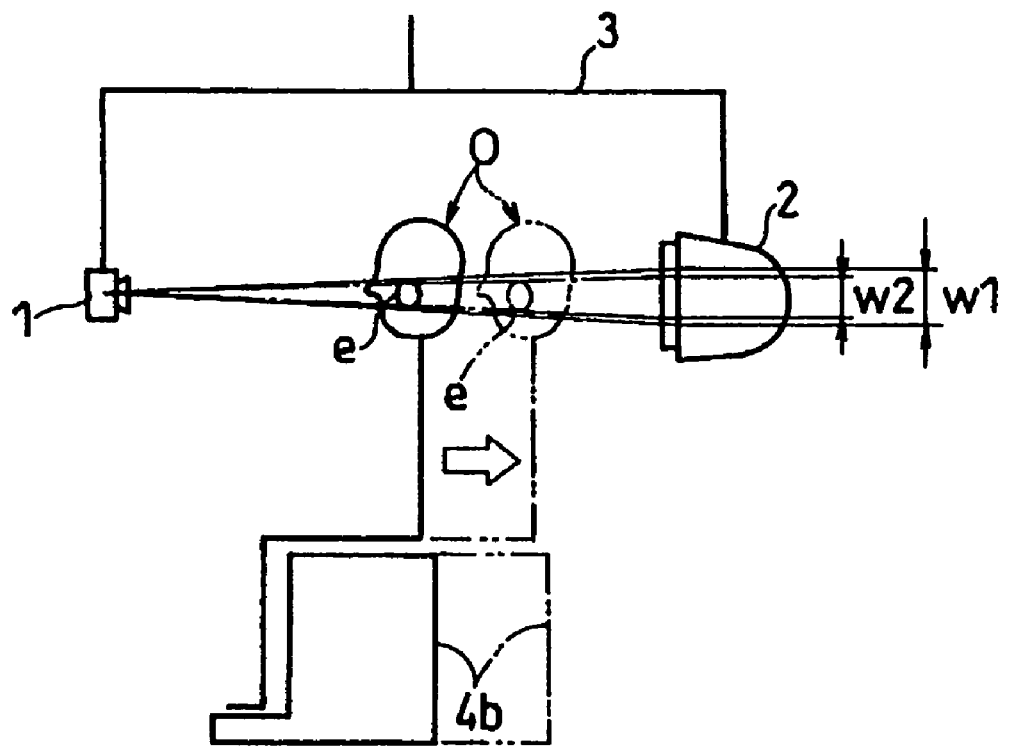
FIG. 6 is a diagrammatical operation view showing a principle of enlarging the proportion of scout image.

Therefore, as shown in FIG. 6, the chair 4b is moved from a normal position into the two-dimensional X-ray image sensor 2 side, thereby reducing the size of scout image detected by the two dimensional X-ray image sensor 2 and enlarging the projection area. The proportion change means H is carried out by moving the rotary means 3 other than moving the chair 4b. If the size of the target region "e" of the object O on the scout image is assumed as w1, it becomes w2 on the scout image of the target region "e" wherein the chair 4b is moved backward.

In this case, w1 is larger than w2, therefore, the occupying ratio of the target region "e" against the whole size of the scout image is made smaller, so that the projection area as the scout image is considered to be enlarged. The enlarged ratio of the projection area is w1/w2. For easy understanding, the target region "e" of the object O is at a position where a tomogram is obtained and the chair 4b is moved from the normal position to be near the two-dimensional image sensor 2 in the above-mentioned embodiment. However, the target region "e" of the object O may be controlled to be near the two-dimensional X-ray image sensor 2 at the time of obtaining a scout image.

Figure 7:
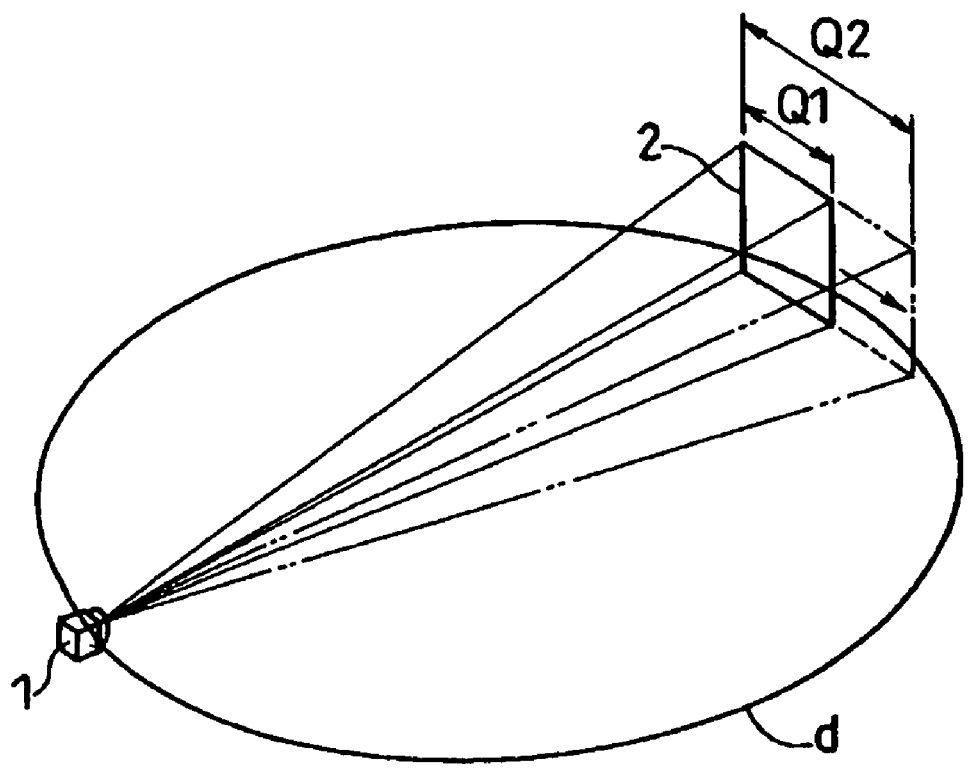
FIG. 7 shows an operation view showing a principle of a scanning imaging means.

Next, a scan imaging means I is explained. The purpose of the scan imaging means I is to enlarge a scout image like the above-mentioned proportion setting means 12. That is, the scan imaging means I has a function that a fluoroscopic image is obtained by the preliminary imaging means D while shifting the two-dimensional X-ray image sensor 2 in horizontal or vertical to the X-ray generator 1. More specifically, as shown in FIG. 7, the two-dimensional X-ray image sensor 2 is slid horizontally by means of a suitable moving means in case of obtaining a scout image. Thus, the width of image is enlarged from Q1, which is the width at stationary state, to Q2 and its enlarged ratio is Q2/Q1. In FIG. 7, the object O is omitted to be shown for easy understanding.

Then, the characteristics of the X-ray CT apparatus according to the present invention are described. For positioning the X-ray generator 1, the object O, and the two-dimensional X-ray image sensor 2 in case of obtaining two scout images sc1 and sc2, there seems to be a prominent angle on a scout image depending on the projection area, therefore, it is well advised to pre-set the projecting direction in advance (for example, "a" degree or "b" degree is preset in case of auditory ossicle). If there is any prominent angle on a scout image by the operator's knowledge, the operator preferably sets the angle before starting to obtain a scout image. Other than those cases, if a recommended projection angle is predetermined, operations can be rapidly preceded without suffering an angle.

In a prior X-ray CT apparatus, back and forth, right and left or up and down optical marker showing the height of the rotary center and the two-dimensional image sensor has been used for positioning in order to determine the projection area, however in this case, the optical marker is projected on the object's surface and the projection area in the object body has to be supposed from the position, thereby accurate positioning being difficult.

According to the present invention, a scout image is obtained from two directions before executing CT imaging, these images are shown on a display (display monitor E), a target point m is pointed (clicked) at an area of which CT image is to be obtained. A space point on the area for CT imaging exists on a line connecting the pointing position and the focus of conical X-ray beam, therefore, the space point is determined on the area for CT imaging if there is at least two such lines. The rotary means 3 or the chair 4b is moved in such a manner that the determined point becomes the rotary center in case of CT imaging, thereby enabling CT imaging at a desired position.

Figure 15A:
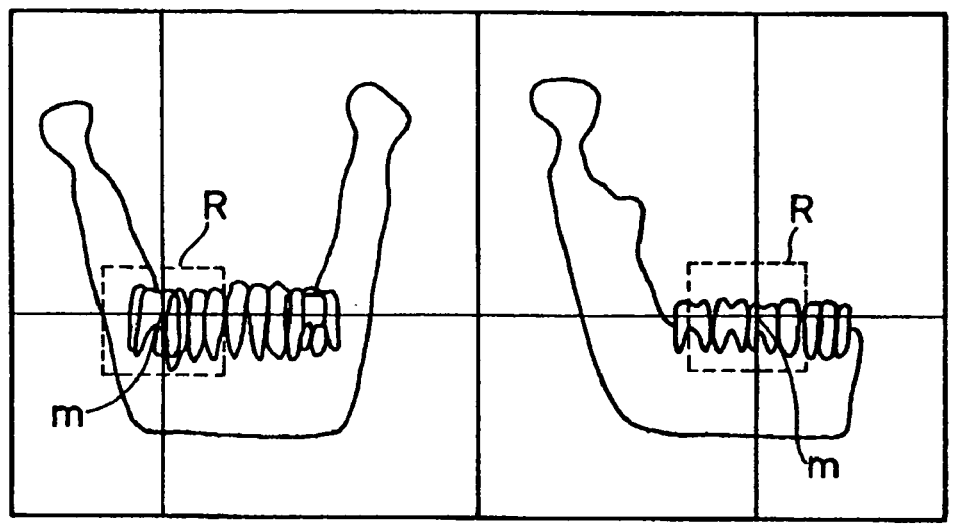
FIG. 15a is a conceptual view showing a display of a fluoroscopic image and FIG. 15b is a conceptual view showing a tomogram of a target region.
Figure 15B:
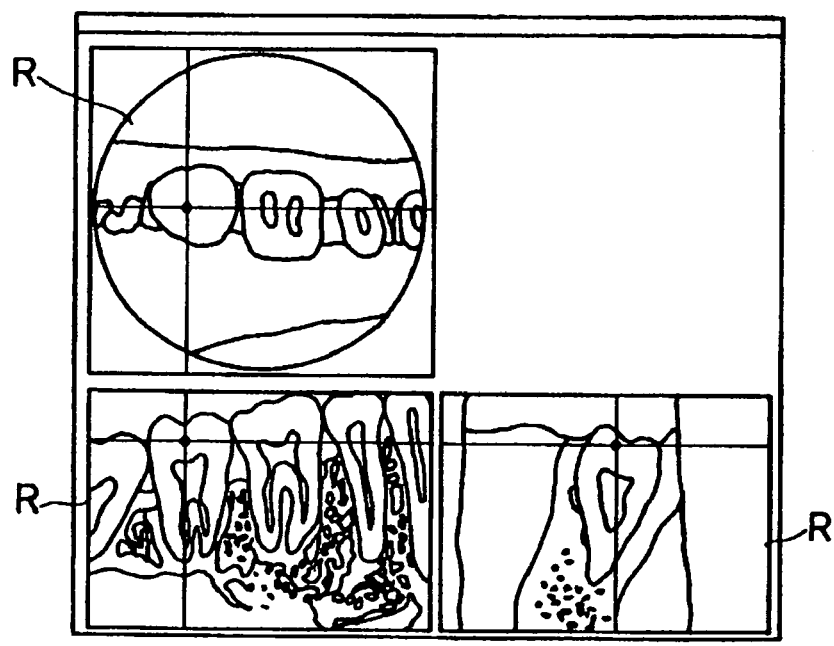

FIG. 15a is a conceptual view showing a display of a fluoroscopic image and FIG. 15b is a conceptual view showing a tomogram at a target region obtained based on the target region determined on the fluoroscopic image.

As shown in FIG. 15a, if a cursor is moved in order to specify the target point "m" shown on the plural fluoroscopic images obtained at a preliminary imaging by the above-mentioned preliminary imaging means D, the rotary means 3 is rotated at a predetermined position corresponding to its position following the above-mentioned procedures, tomography, that is an X-ray CT imaging, is executed, and the obtained tomograms are shown as a tomogram quarried out in X, Y, and Z direction respectively as shown in FIG. 15b. Such a method of taking out and showing a tomogram in X, Y, and Z direction has been disclosed in JP-A-2002-11000 by the applicant of the present invention and can be employed as one embodiment of the present invention.

Figure 17A:
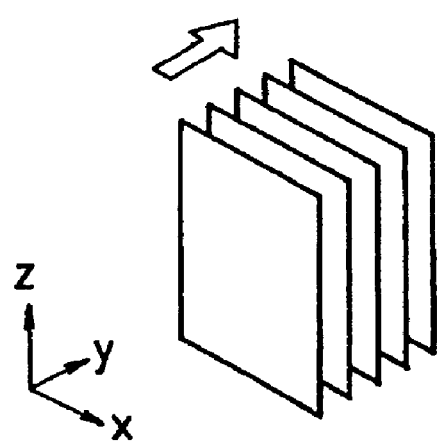
FIG. 17a shows an example in which images are quarried out in one direction.
Figure 17B:
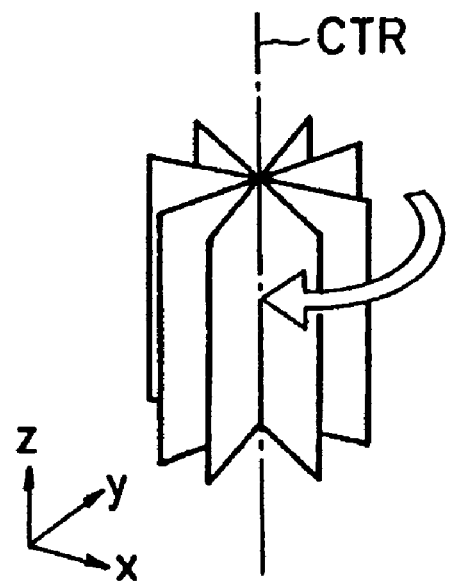
FIG. 17b shows an example in which plural images are quarried out around the center axis.

As mentioned above, an embodiment wherein the images are quarried out at a fixed space at least in one direction among X, Y, and Z-axis direction as shown in FIG. 17a, however, a method may be applied such that an axis CTR is determined in a projection interest area and plural images are quarried out by executing image processing around the axis CTR as shown in FIG. 17b.

The above-mentioned plural fluoroscopic images and the tomograms obtained based on these fluoroscopic images are stored in the image storage means K, thereby being able to be optionally invoked by the image invoking means L. Further, the plural fluoroscopic images and the tomograms obtained by the fluoroscopic images are related each other and stored in the image storage means K. Therefore, while invoking any one of fluoroscopic images or tomograms is invoked, its relating image is invoked by the image invoking means L.

Figure 16:
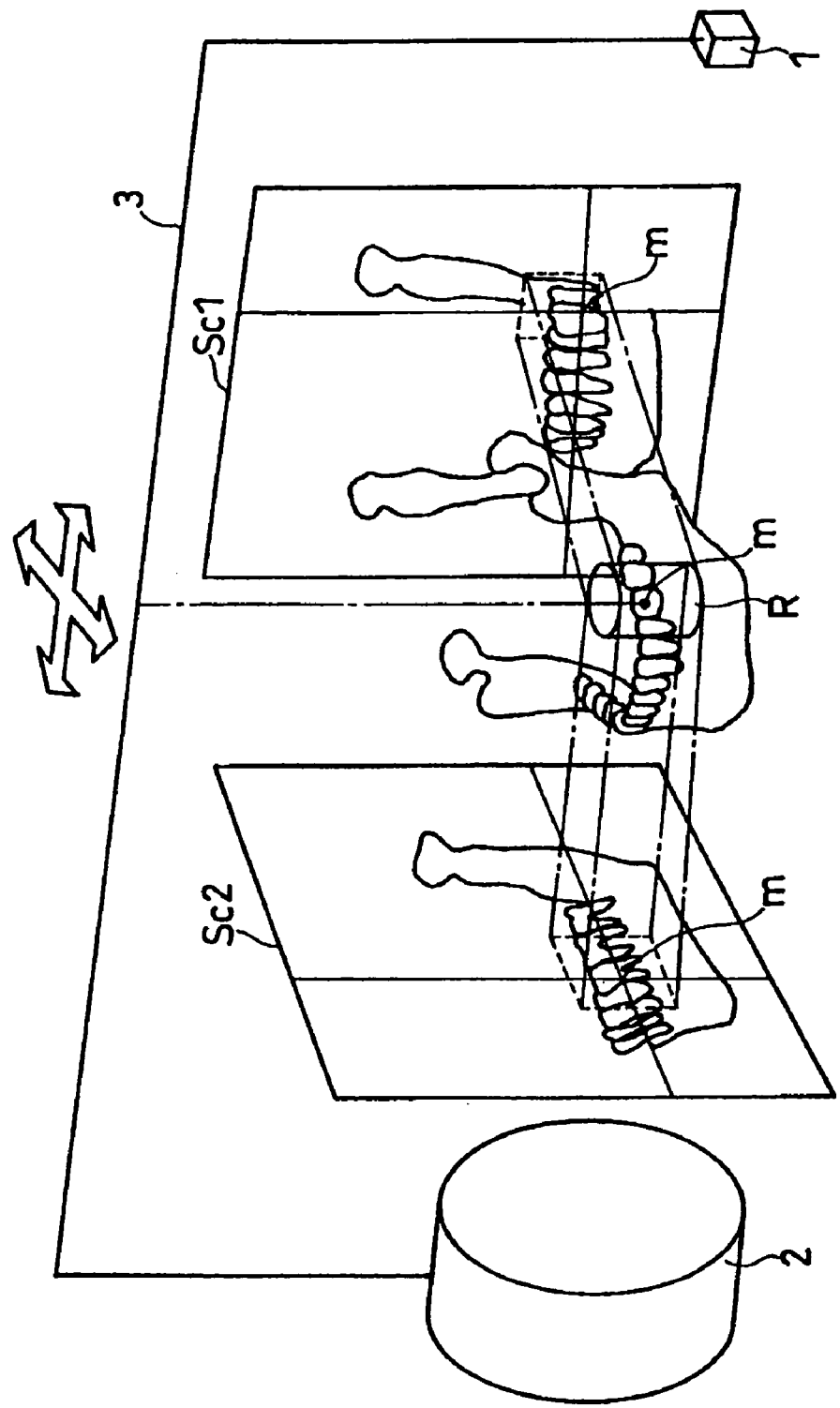
FIG. 16 is an image view for conceptually understanding from obtaining the fluoroscopic image to obtaining the tomogram.

The fluoroscopic image and the tomogram may be shown on the same screen, or plural ones of fluoroscopic images or tomograms are invoked and shown in small size as a sum-nail and on selecting any one of them, the corresponding other image may be shown. FIG. 16 is an imaginary view for conceptually understanding the step of specifying the projection interest area which is an object of X-ray CT imaging based on a fluoroscopic image and the step of obtaining a tomogram by CT imaging. Name and function of each member are omitted because they are redundant, so that only their reference numerals are shown in FIG. 16.

For reference, an actual calculation method of positioning according to the conical X-ray beam CT apparatus is explained.

1. Scout in two directions is basically for determining one point in a space by specifying a point on a projection image obtained from two directions.

2. Determining the point on the scout image is equivalent to determining a straight line in a space. This line connects a point on the image sensor and the focus.

3. For obtaining a scout image with MCT apparatus, the position of the chair may move in parallel on the (X, Y) plane from a standard point. The Z-coordinate of the focus, and the distance between the focus and the image sensor aren't changed.

4. When the chair is moved in parallel, the positional relation between the imaging system (focus, rotary center, and screen) and the object is relatively changed. It seems to be equivalent to that the imaging system is moved in parallel in a reverse direction of the chair while the chair is fixed. This is equivalent to the above-mentioned 2 in which the straight line on a space is moved in parallel.

5. Because there are two scout images, two straight lines exist in a space. These two lines are required to be intersected, so that they are not independent. User may optionally specify the X-coordinate on each scout image, however, when on the Z-coordinate, if one is specified, other is automatically determined.

Figure 13:
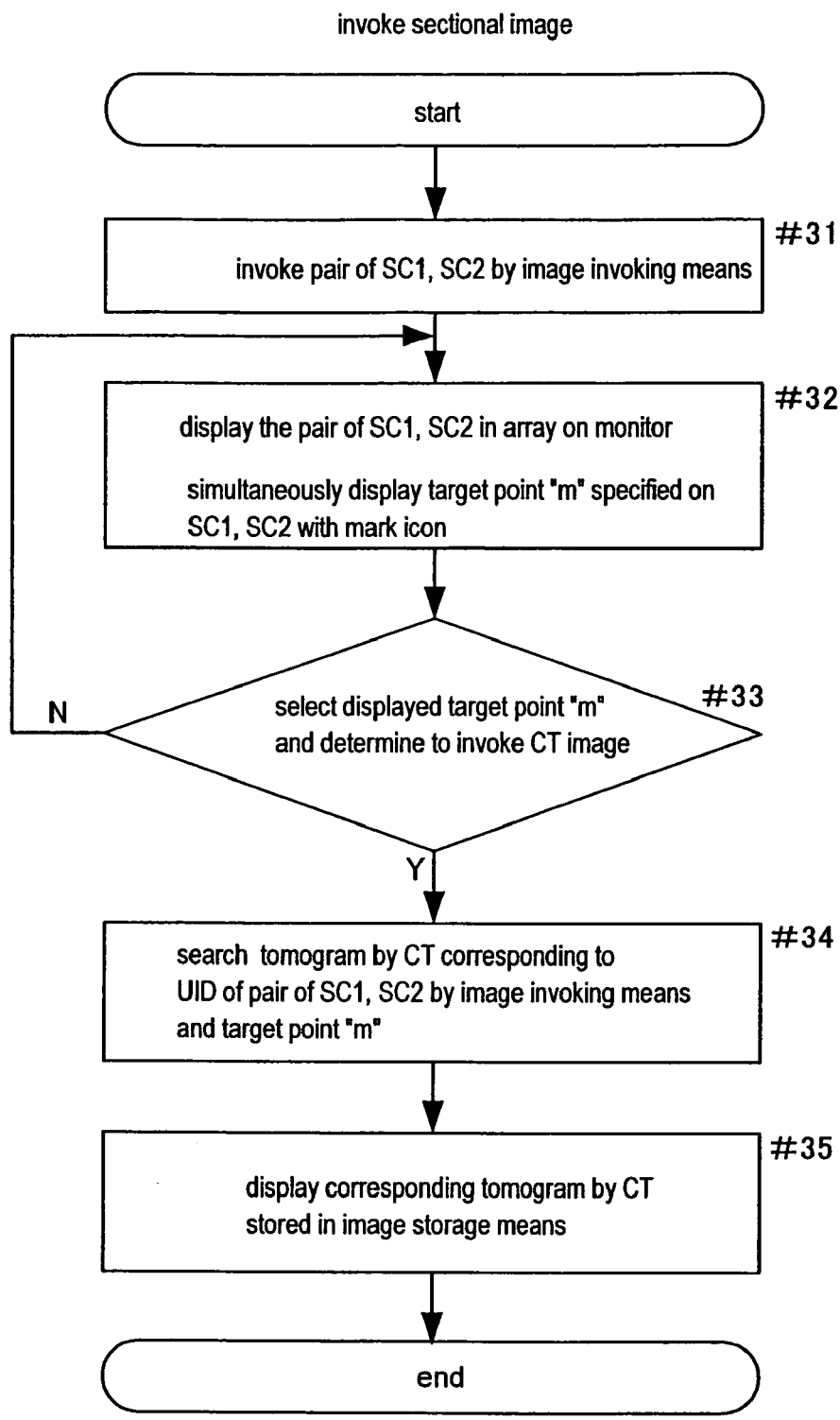
FIG. 13 is a flow chart showing a subroutine invoking a tomogram from a fluoroscopic image.
Figure 14:
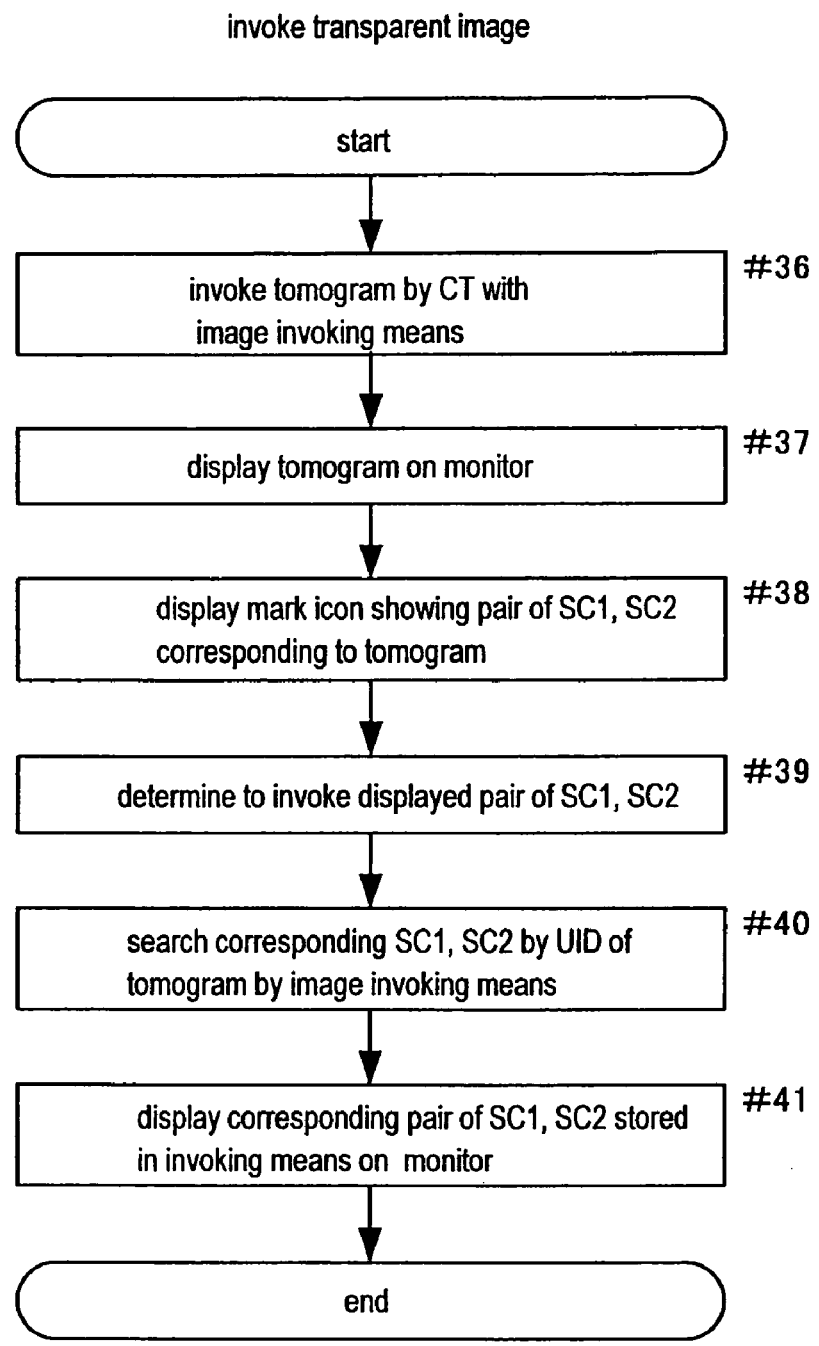
FIG. 14 is a flow chart showing a subroutine invoking a fluoroscopic image from a tomogram.

For reference, FIG. 9–FIG. 13 show a flow chart which shows a series of operation procedures with the CT apparatus from obtaining scout images to obtaining tomograms (main routine: step #1–step #30). In FIG. 9–FIG. 12, procedures are successively progressed and thereafter, with a function of the image invoking means L, the subroutine for invoking a tomogram (CT image) from a fluoroscopic image (scout image) (step #31–step #35) as shown in FIG. 13 or the subroutine for invoking a fluoroscopic image from a tomogram (step #36–step #41) as shown in FIG. 14 is selected, thereby continuing procedures.

Supplemental explanations are described here. "Other mode" in step #1 is for example CT imaging. "UID" in steps #15, #23, #30, #34, and #40 indicates "Unique ID" which is a unique ID number allotted to each image. The scout image sc1 in step #2 is a first fluoroscopic image and the scout image sc2 in step #7 is a second fluoroscopic image. In the following steps, the scout images sc1 and sc2 have the same meaning.

The subroutine for invoking tomogram (see FIG. 13) and the subroutine for invoking fluoroscopic image (see FIG. 14) are able to be executed after the steps #1–#30 are finished. The target point "m" at the step #32 may be plural. Namely, plural target points "m" may be specified on the same pair of fluoroscopic images. The rotary means 3 is shown as a rotary arm in the flow chart.

The routine V (#24-1–#24-7) for defining the step #24 in the main routine is supplementary explained. The two-dimensional position of the target point "m" of the scout image sc1 shown on the monitor is calculated as a two-dimensional position information shown with pixel (step #24-1). Then, the three-dimensional position information of the target point "m" on the detection plane of the two-dimensional X-ray sensor corresponding to the two-dimensional position information value by the pixel and the rotary arm angle, namely the tree-dimensional position information on the actual three-dimensional space of the detection position of the target point "m" on the detection plane of the two-dimensional X-ray image sensor, is calculated (step #24-2). The three-dimensional data of the straight line L100 that passes through the target point "m" from the X-ray generator is calculated from thus calculated three-dimensional position information, the rotary arm angle, and the position information of the X-ray generator (step #24-3).

Next, the two-dimensional position of the target point "m" of the second scout image sc2 shown on the monitor is calculated as a two-dimensional position information with pixel (step #24-4), the three-dimensional position information of the target point "m" on the detection plane of the two-dimensional X-ray sensor corresponding to the two-dimensional position information value with pixel and the rotary arm angle, namely the tree-dimensional position information on an actual three-dimensional space of the detection potion of the target point "m" on the detection plane of the two-dimensional X-ray sensor is calculated (step #24-5). The tree-dimensional data of the straight line L200 formed with X-ray passing through the target point "m" from the X-ray generator is calculated from the calculated three-dimensional position information, the rotary arm angle, and the position information of the X-ray generator (step #24-6). Thus, the tree-dimensional position (target point "m") which is an intersection of the line L100 and the line L200 is calculated (step #24-7).

Other Embodiment

Figure 8:
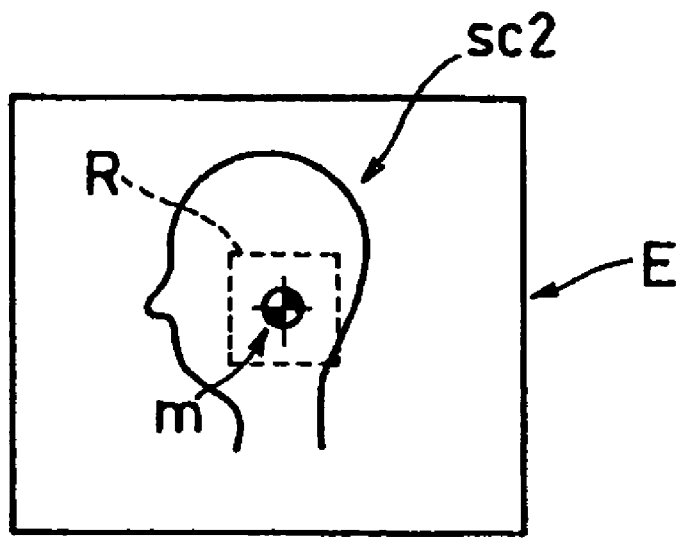
FIG. 8 is an operation view showing a concept of a projection area display control means.
Figure 9:
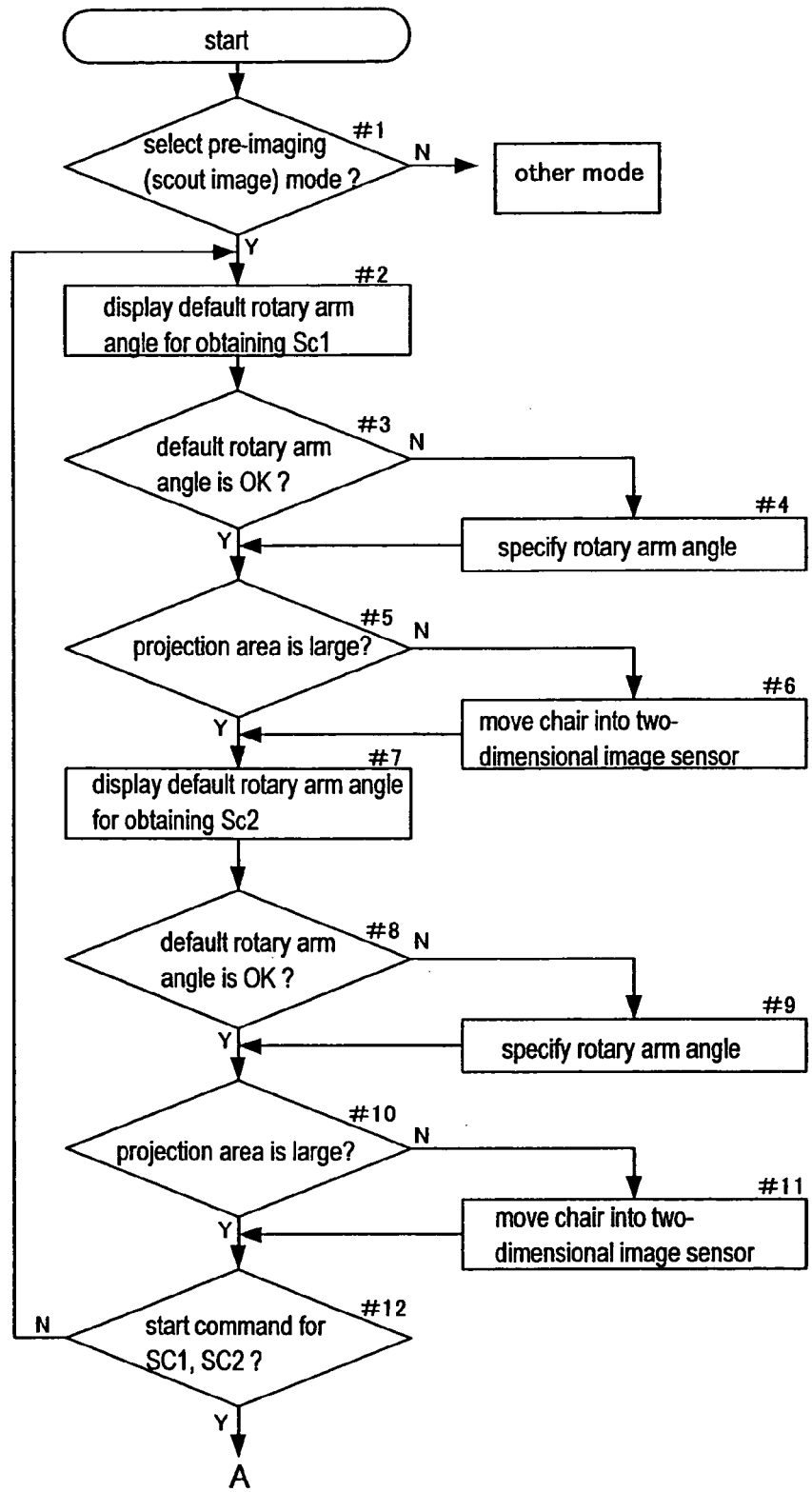
FIG. 9 is a flow chart 1 showing sequential operations from a preliminary imaging to a main imaging.
Figure 10:
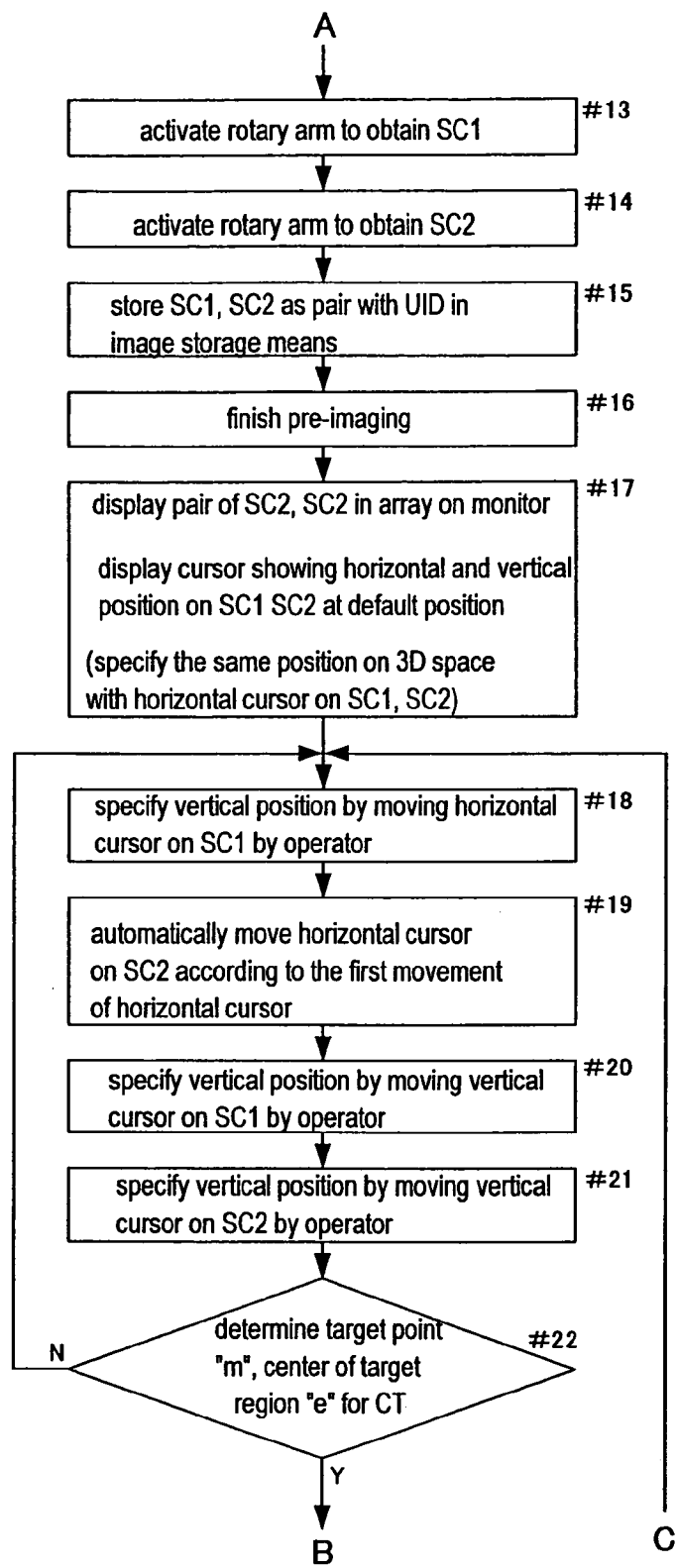
FIG. 10 is a flow chart 2 showing sequential operations from a preliminary imaging to a main imaging.
Figure 11:
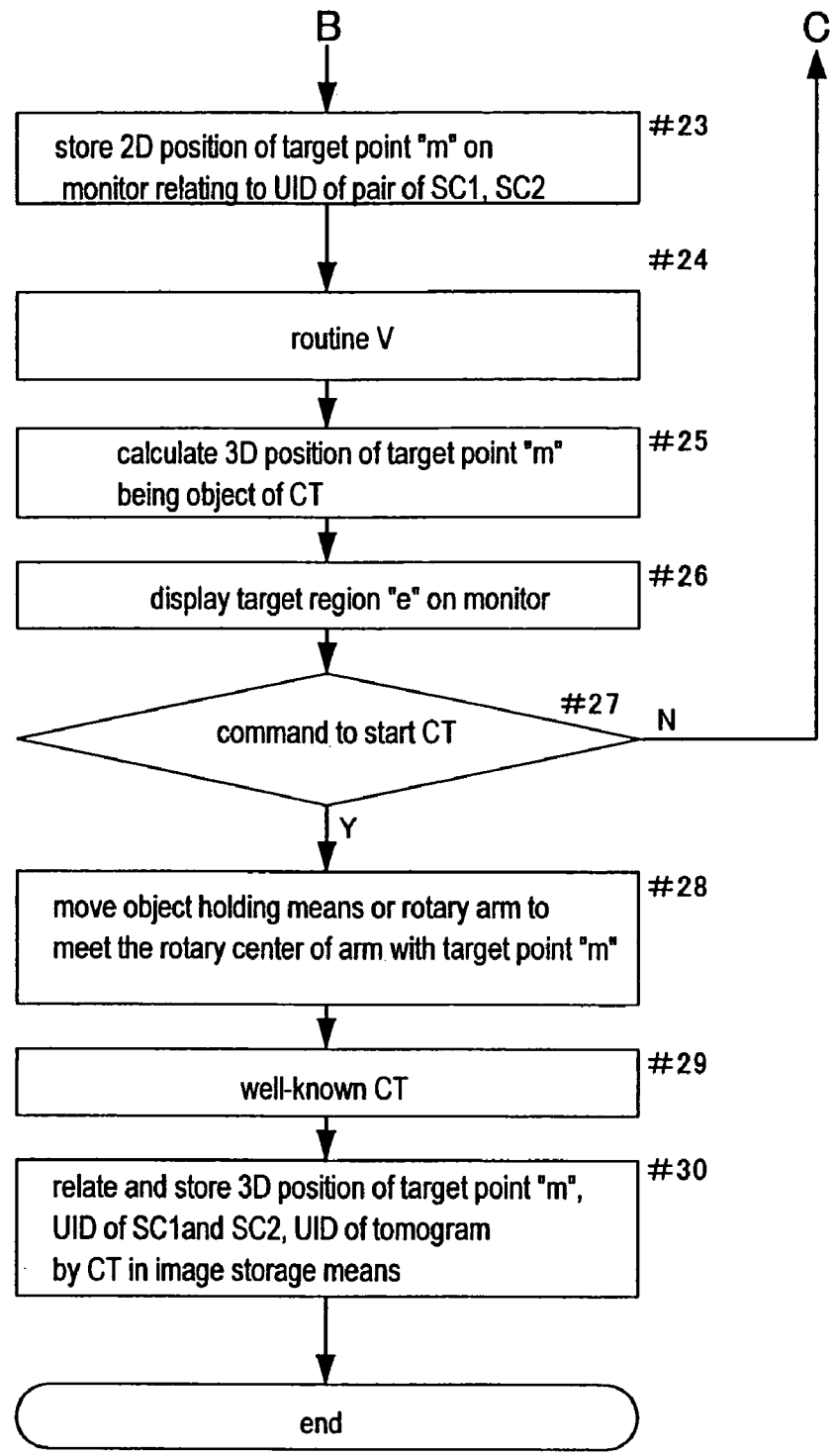
FIG. 11 is a flow chart 3 showing sequential operations from a preliminary imaging to a main imaging.
Figure 12:
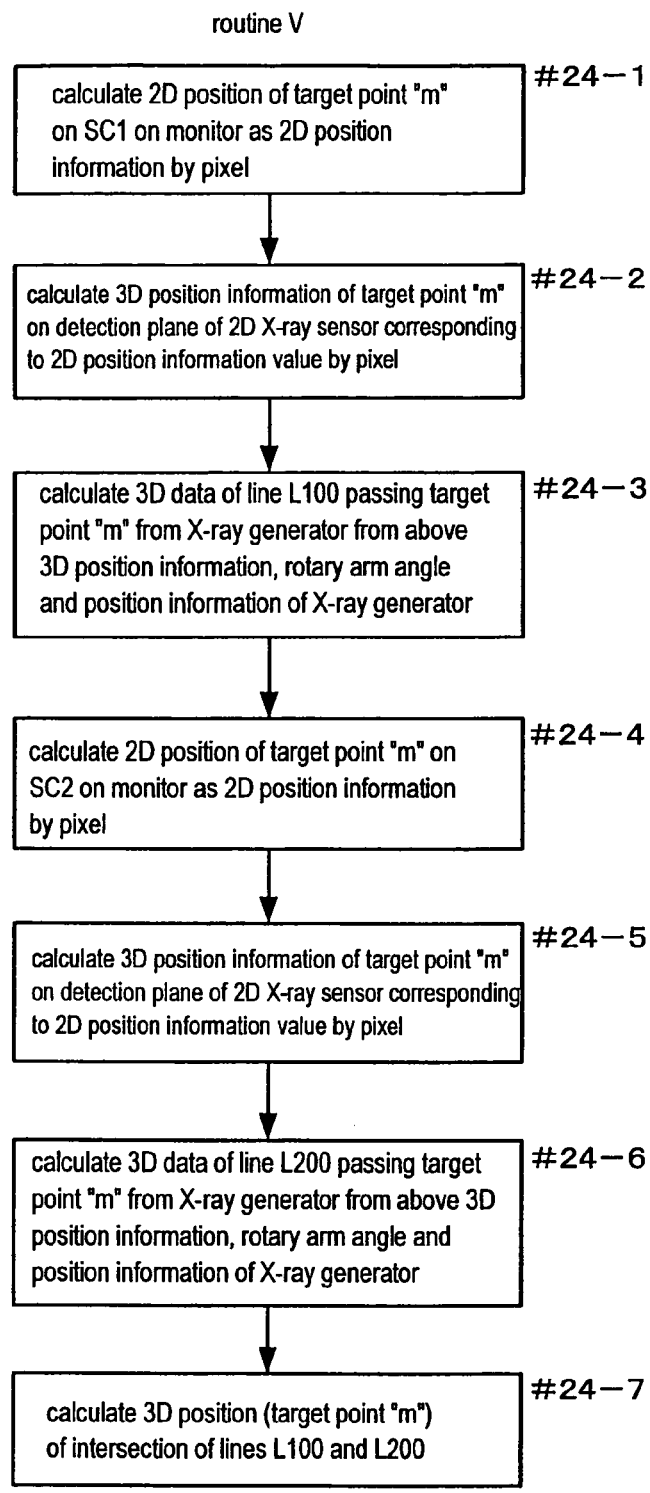
FIG. 12 is a flow chart showing a routine V.

<1> A projection area display control means M may be provided such that the projection area of the tomogram relating to the obtained three-dimensional position when the tree-dimensional position is obtained by the preliminary imaging means D is displayed on the fluoroscopic image shown on the display monitor E. Namely, as shown in FIG. 8, second pointing (click) on the target point on the second scout image sc2 determines the three-dimensional position of the target point "m", accordingly the projection area R of the tomogram (rectangle with broken line in FIG. 8) which is obtained by X-ray CT imaging based on the obtained three-dimensional position data is shown on the display screen. It is advantageous that the projection area R is shown on the screen together with a dimensional display such as 400 mm width and 300 mm long.

Figure 5:
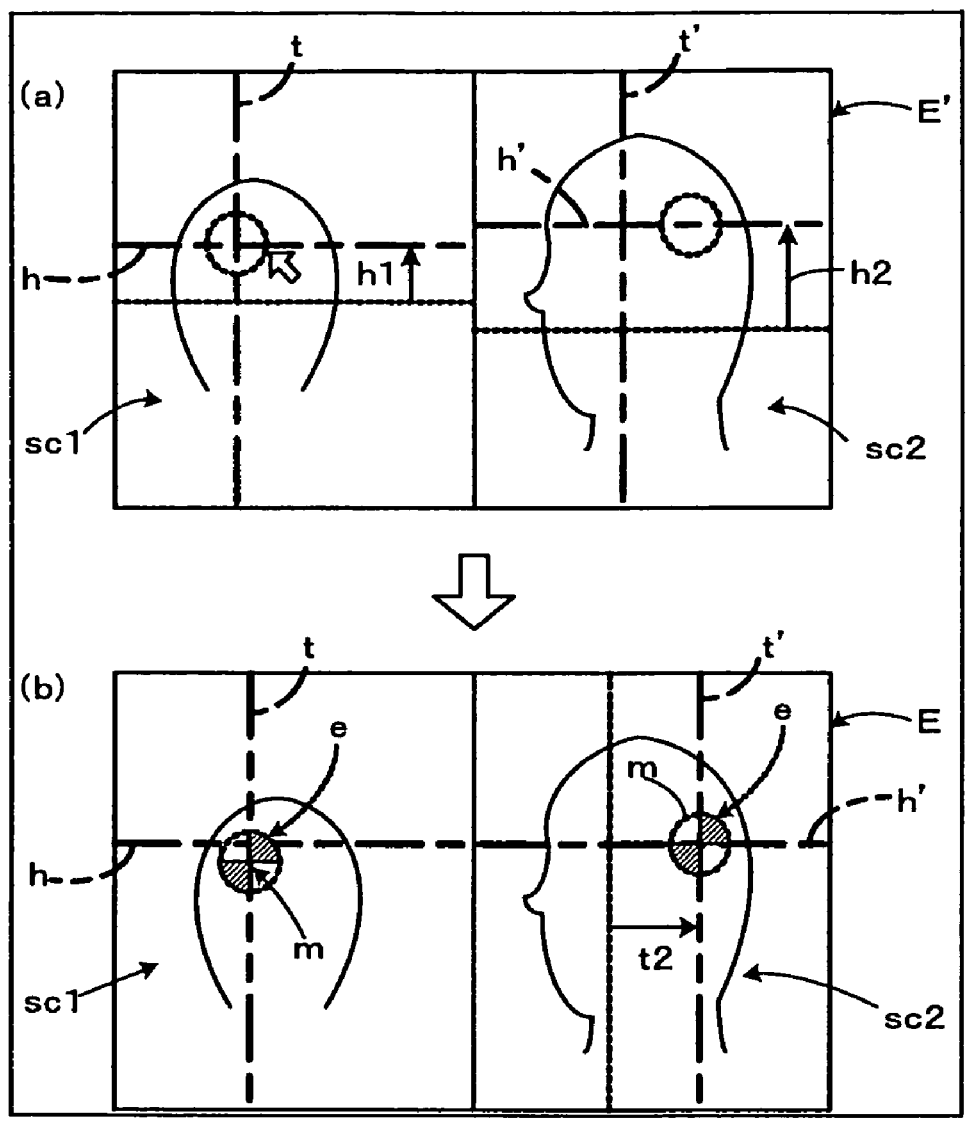
FIG. 5 shows how the position is determined by means of two scout images that have different projection ratio.

<2> Positioning of the target point m by means of a cross-hairs cursor when the scout images sc1 and sc2 with different imaging proportion is carried out as shown in FIG. 5. Namely, when the first scout image sc1 is small and the second scout image sc2 is large, the cursor is moved with the distance h1 from the dotted line to the solid line in order to determine the horizontal position "h" on the left screen, and the cursor is moved with the distance h2 on the second scout image sc2 at the left screen. Namely, the movement of the cursor on the second scout image sc2 at right is enlarged.

Next, when the cursor is moved into the second scout image sc2 as shown in FIG. 5b, is further moved around the center of the target region "e" on the second scout image sc2 and is clicked at the position, the vertical positions t, t' which are right and left positions are specified, thus the three-dimensional position of the target region "m" is artificially determined. Such a series of positioning operation is executed by the positioning operation means J. Namely, even if the pace of expansion is different, the proportion of the cursor movement is varied accordingly, thereby enabling to position the target point "m" without having any troubles.

In the above-mentioned embodiments, the shape of the cursor is shown such that the vertical position and the horizontal position are simultaneously shown. However, appropriate variations are possible like only the vertical position is specified with a vertical cursor on the first scout image and a horizontal cursor is appeared on the second scout image both on the first and second scout images so as to arrange the position between the first scout image and the second scout image; or an arrow pointer is simply shown on both scout images.

Examples of cursor are shown in FIG. 18. FIG. 18a shows a circular cursor for specifying the target region "e" or the target point "m". It goes without saying that other shapes other than the circle may be employed. FIG. 18b shows a cross-hair cursor lacking its center for specifying the target region "e" or the target point "m". It goes without saying that the number of lines isn't limited other than the cross joint.

Figure 18A:
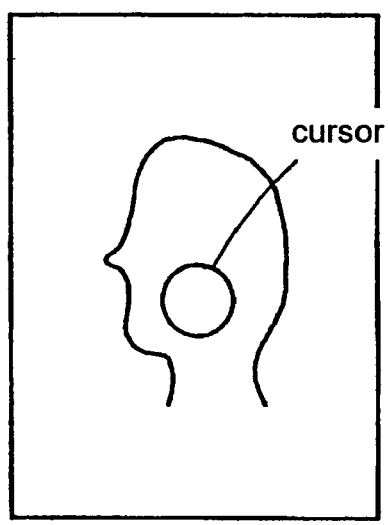
FIG. 18a shows an example of a circle cursor.
Figure 18B:
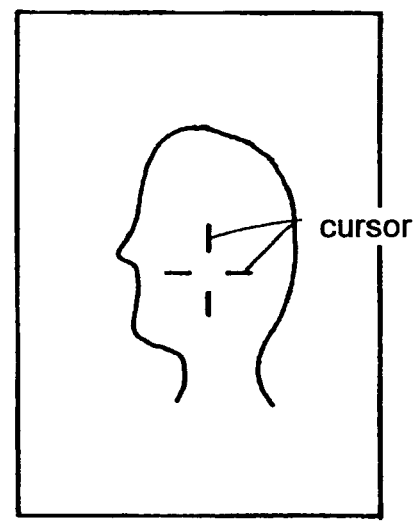
FIG. 18b shows an example of a cross-hairs cursor.
Figure 18C:
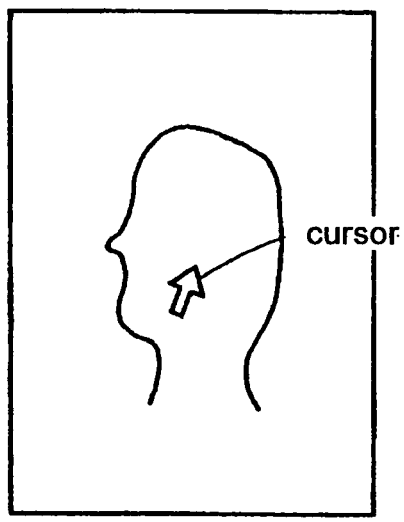
FIG. 18c shows an example of an arrow cursor.
Figure 18D:
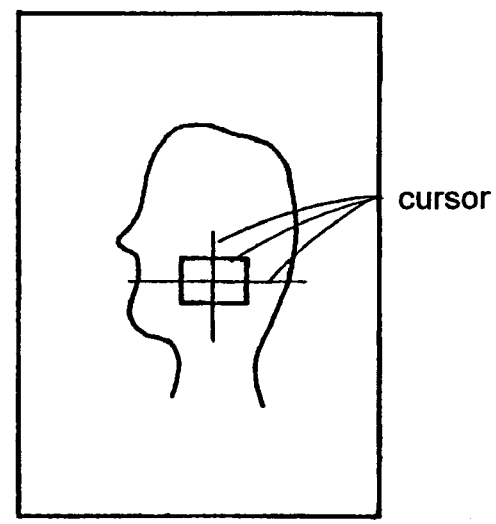
FIG. 18d shows an example when a square cursor and a cross-hairs cursor are combined.

FIG. 18c shows an embodiment with an arrow cursor for specifying the target region "e" or the target point "m". Dot or other pointer than an arrow may be used. FIG. 18d shows an embodiment in which the rectangular cursor and the above-mentioned cross-hair cursor are used in combination. It goes without saying that the combination and the pointer types are variable.

In FIG. 18a and FIG. 18b, although it is difficult to accurately specify the target point "m" with its center, it is advantages that the image around the target point "m" isn't covered with the cursor. In FIG. 18c and FIG. 18d, the image around the target point "m" is covered with the cursor, however, the target point "m" can be specified with its center.

<3> The number of the scout images may be more than three in order to more accurately determine the target point "m", in short, at least two different scout images are required to be obtained.

<4> The proportion change means H may be constructed such that the chair 4b, namely the object O, is fixed and the main frame 10 is moved.

<5> The scan imaging means I may be constructed such that the two-dimensional X-ray image sensor 2 may be moved vertically or diagonally or the X-ray generator 1 may be shifted in parallel.

<6> The three-dimensional position of the target point "m" may be obtained using plural scout images, other than with click operation, namely a manual operation, in such a manner that several conditions like change in the color tone or in transition of the diseased part on the image are input into the control means 7 in advance, the control means has a function that the area with more than a predetermined change is automatically recognized as a target region, so that it is possible to employ a control means (system) in which the target region is automatically inferred from more than two scout images.

The invention claimed is:

1. An X-ray computer tomography apparatus wherein a conical X-ray beam is radiated on a local area of an object while a rotary means with an X-ray generator and a two-dimensional X-ray image sensor faced to each other is rotated relative to the object which is disposed between the X-ray generator and the two-dimensional X-ray image sensor, and the obtained image is shown, said X-ray computer tomography apparatus comprising:
   a preliminary imaging means for imaging said object under plural positional conditions wherein positional relations among said X-ray generator, said object and said two-dimensional X-ray image sensor are varied;
   a positioning operation means for specifying the two-dimensional position of a target region in said object on plural fluoroscopic images, which are obtained by said preliminary imaging means and shown on a display means in array, with a crosswise cursor for specifying horizontal position and a vertical cursor for specifying longitudinal position, wherein when the horizontal position is being specified with said crosswise cursor, the same horizontal position is being positioned on other fluoroscopic images;
   a processing means for obtaining a three dimensional position of said target region in said object by calculating a two-dimensional positional data of said target region in said object;
   a position adjustment means for adjusting said positional relation among said X-ray generator, said object and said two-dimensional X-ray image sensor in such a manner that the rotary center comes to said three dimensional position of said target region in said object obtained from said processing means;
   a main imaging means for obtaining a tomogram of said object while said rotary means and said object are relatively rotated after adjusting with said position adjustment means;
   a display means; and
   an image invocation means having a function for displaying the tomogram in said target region as specified on said display means when said target region in said object is specified on said fluoroscopic image selected from those stored in said image storage means and displayed on said display, and/or a function for displaying the fluoroscopic image used for obtaining said region corresponding to the tomogram displayed on said display means while said tomogram selected from said plural tomograms stored in said image storage means is displayed on said display means.

2. The X-ray computer tomography apparatus as set forth in claim 1, further comprising:
   a proportion change means capable of changing the proportion of the distance between said object and said two-dimensional X-ray image sensor to the distance between said X-ray generator and said two-dimensional X-ray image sensor; and
   a proportion setting means for making said proportion at the time of obtaining a fluoroscopic image smaller than at the time of obtaining a tomogram.

3. The X-ray computer tomography apparatus as set forth in claim 1, further comprising a scan imaging means for shifting said two-dimensional X-ray image sensor in a direction orthogonal to the conical X-ray beam radiated from said X-ray generator while said preliminary imaging means is imaging a fluoroscopic image.

4. The X-ray computer tomography apparatus as set forth in any one of claims 1, 2 and 3, further comprising:
   a display means for showing plural fluoroscopic images on a screen in array; and
   a positioning operation means for specifying said three-dimensional position in such a manner that a target region is first directed on any one of said fluoroscopic images shown on the display means with one cursor in the crosswise and/or vertical direction then the target region is secondly directed on another fluoroscopic images other than said fluoroscopic image with the other cursor or cursors in the vertical and/or crosswise direction.

5. The X-ray computer tomography apparatus as set forth in claim 1, further comprising a control means for indicating a projection area of said target region specified by said three-dimensional position on the fluoroscopic image displayed on said display means when said three-dimensional position of said target region is obtained from said processing means.

6. An X-ray computer tomography method wherein a conical X-ray beam is radiated on a local area of an object while a rotary means with an X-ray generator and a two-dimensional X-ray image sensor faced to each other is rotated relative to the object which is disposed between the X-ray generator and the two-dimensional X-ray image sensor, and the obtained image is shown, said X-ray computer tomography method comprising the steps of:
   imaging said object under plural positional conditions wherein positional relations among said X-ray generator, said object and said two-dimensional X-ray image sensor are varied;
   specifying the two-dimensional position of said target region in said object on plural fluoroscopic images of said object shown in array with a crosswise cursor for specifying horizontal position and a vertical cursor for specifying longitudinal position, wherein when the horizontal position is being specified with said crosswise cursor, the same horizontal position is being positioned on other fluoroscopic images;

obtaining a three dimensional position of said target region in said object by calculating a two-dimensional positional data of said target region in said object which is determined on plural fluoroscopic images obtained by said preliminary imaging means;

adjusting said positional relation among said X-ray generator, said object and said two-dimensional X-ray image sensor in such a manner that the rotary center comes to said three dimensional position of said target region in said object obtained by a processing means; and obtaining a tomogram of said object while said rotary means and said object are relatively rotated after adjusting said positional relation.

* * * * *